(12) United States Patent
Rini

(10) Patent No.: US 6,415,916 B1
(45) Date of Patent: Jul. 9, 2002

(54) BLISTER PACK FOR ARTIFICIAL TEETH OF PROSTHETIC USE

(76) Inventor: Guido Rini, Via Caledonie 9, 74020 Lama TA (IT)

(*) Notice: Subject to any disclaimer, the term of this patent is extended or adjusted under 35 U.S.C. 154(b) by 0 days.

(21) Appl. No.: 09/719,702

(22) PCT Filed: Jun. 16, 1999

(86) PCT No.: PCT/IT99/00220
§ 371 (c)(1),
(2), (4) Date: Dec. 14, 2000

(87) PCT Pub. No.: WO00/06463
PCT Pub. Date: Feb. 10, 2000

(30) Foreign Application Priority Data

Jul. 27, 1998 (IT) .................... RM98U0200

(51) Int. Cl.[7] ................................ A61C 19/10
(52) U.S. Cl. .................. 206/83; 206/459.5; 433/26
(58) Field of Search ............. 206/83, 63.5, 581, 206/368, 369, 461, 459.5, 531, 532, 534; 433/25, 26, 77, 79

(56) References Cited

U.S. PATENT DOCUMENTS

| | | | | | |
|---|---|---|---|---|---|
| 2,111,095 | A | * | 3/1938 | Evans | 206/83 |
| 2,554,044 | A | * | 5/1951 | McNeill | 206/83 |
| 3,018,884 | A | * | 1/1962 | Fritz | 206/83 |
| 3,894,531 | A | | 7/1975 | Saunders, Jr. | |
| 4,979,611 | A | * | 12/1990 | Bollinger et al. | 206/83 |
| 5,261,815 | A | | 11/1993 | Pozzi | |
| 5,653,589 | A | * | 8/1997 | Kleinmann | 433/26 |
| 5,782,632 | A | | 7/1998 | Foser | |
| 5,791,478 | A | | 8/1998 | Kalvelage et al. | |

* cited by examiner

Primary Examiner—Luan K. Bui
(74) Attorney, Agent, or Firm—Ladas & Parry

(57) ABSTRACT

A blister pack (10) for artificial teeth of prosthetic use comprises: a first layer (11) containing the artificial teeth (3), having a plural of raised regions (13) in correspondence with the artificial teeth; a second layer (12) placed below the first layer and welded therewith, having a plurality of punching regions (16) apt to be punched upon pressure onto the raised regions; and a plurality of removable elements (14) identifying the blister pack, placed along removal regions (15) of the second layer.

10 Claims, 3 Drawing Sheets

BLISTER PACK FOR ARTIFICIAL TEETH OF PROSTHETIC USE

DESCRIPTION

The present invention relates to a blister pack of artificial teeth of prosthetic use.

Blister packs for medical use are already known in the art.

From U.S. Pat. No. 3,894,531 a skin patch test device with a peelable strip is known. Such skin patch comprises a peelable strip with a double function. A first function is that of enabling the medical preparation to be contacted to the skin of the patient after peeling of the strip. A second function of the peelable strip is that of containing information relating to the medical preparations. A first disadvantage of the peelable strip is that it can be peeled only when using the test device. A second disadvantage lies in that the information carried on the strip can be used only by a single user.

Also boxes for containing tooth-related systems are known in the art.

From U.S. Pat. No. 5,261,815 a dental tooth shade/hue matching reference system is known, for providing artificial teeth with lifelike shade and hue, or for matching the shade and hue of an artificial tooth with the shade and hue of one's natural teeth. The box containing such a system is neither apt to contain blister packs, nor does it show a transparent cover for enabling optical identification of its contents.

A packing for artificial teeth is already known in the state of the art and it shall be disclosed hereinafter with reference to FIGS. 1 and 2.

In FIG. 1 a strip 1 made of transparent plastic material is shown in a perspective view. A wax bed 2 has been molded in the substantially central region of strip 1. On such bed 2 a set of artificial teeth is placed, held in position by the wax solid state; in the example of FIG. 1 the eight upper or lower diatoric elements (i.e. the molars) are shown, generically indicated with 3. A similar placement can be provided for the six upper or lower incisors. The wax whereon the artificial teeth are placed stays soft enough to enable the manual detachment of these teeth for their subsequent employ.

At the sides of the wax bed 2 two raised ending elements 4 are present, apt to bear printed information, shown in figure with numbers and letters, pertaining the colour and the shape of the teeth, so as to enable the various users to spot the features of the product. In fact, once manufactured the lots of strips are supplied to the trader, and from him to the dental technician and then to the dentist. To this end, there subsists the need to comply with the legal liability of the product traceability. This is carried out by the indication and the specification of the product brand, type, lot number and manufacture date onto the registers, documents and/or working forms provided for the purpose. This information shall be followed by the manufacturer as well as by the trader and lastly by the dental technician. The aforedescribed state-of-the-art strips enable the traceability of such indications, by having on their lower surface a number, not shown in FIG. 1, apt to indicate the aforementioned information.

A drawback of such method derives from the very high chance of making mistakes in copying the number, which usually exceeds ten digits. In an attempt to get round such inconvenience, a printing was carried out onto the label, of a series of bar codes in order to represent the aforesaid number. However, it must be noted that the computerized optical reading systems for bar codes are not commonly adopted in dental technology laboratories as well as among small and medium-sized traders of dental wares, who therefore have to carry on anyhow with the manual number copying.

Another drawback of the previous art hereto described derives from the manufacture costs of the strip, very high in comparison to the cost of the product.

A further drawback derives from the poor possibility of automating the packaging process, due to the difficulties in fastening the teeth onto the wax of the strip in a completely automated way; therefore there is an high demand of manpower.

Another further drawback derives from the fact that the strips expose the teeth to any kind of accident, as for instance impacts, scratches and attacks from chemical agents.

Yet another further drawback derives from the fact that the teeth easily detach off the wax of the strip in presence of a strong heat or due to breaking and/or fall of the boxes containing the strips. In such cases the teeth get mixed up very easily, later resulting not easily distinguishable for a correct replacing thereof.

A drawback always associated to the presence of the wax derives from the fact that it attracts and retains the dust.

Another inconvenience derives from the ease of manipulation and replacing of the teeth thus placed, that are therefore easily exposed to possible fraudulent tamperings.

A further inconvenience derives from the manufacturer's reduced possibility of guaranteeing the quality and the technical characteristics of the product. It should be borne in mind that, according to the EEC directive 93/42, the manufacturer is liable for the product packaging as well.

Another even further inconvenience derives from the fact that a very expensive protective box is required. The next FIG. 2 shows in a partial perspective view the modes according to which such a box is manufactured. The box is indicated as a whole with 5 and is intended for the housing and the protection of the strips 1. Such box 5 comprises a cover 6 and a base 7, both to be realized with a carton board of good quality. Along the inner surface of the base 7 a plurality of protruding elements 8 is present, realized in thermoformed plastic and apt to prevent shifting of the strip 1 in a direction parallel to the plane of the base 7. In contact with the cover 6 and on the inner side thereof, a wafer 9 of multilayered paper is also present to prevent instead shifting of the strip 1 in a direction that is orthogonal to the plane of the base 7.

An example of packing similar to that up to now described can be found in U.S. Pat. No. 5,782,632, which however shows the same disadvantages of the packing described with reference to FIGS. 1 and 2.

The present invention overcomes such prior art drawbacks and inconveniences, by providing a blister pack of artificial teeth, comprising:

a plurality of artificial teeth of prosthetic use;

a first layer apt to contain said artificial teeth, comprising a plurality of raised regions next to said artificial teeth;

a second layer placed below the first layer, comprising a plurality of punching regions apt to be punched upon pressure onto the raised regions; and a plurality of removable elements identifying the blister pack, placed onto the second layer.

Preferred embodiments of the present innovation are provided in the claims from 2 to 8.

The present invention further provides a box of artificial teeth, comprising: a plurality of blister packs of artificial teeth for prosthetic use, according to the content of claims 9 and 10.

A first advantage of the blister pack according to the present innovation derives from the fact that the production costs are considerably lower than those of the previous art, assessable in a 70% reduction of the packaging cost.

A second advantage derives from the fact that the packaging times are considerably shorter than those provided for the abovedescribed strip.

Another advantage derives from the fact that now the blister packaging process is carried out in a completely automated way. In fact, the teeth are not manually fastened anymore, but rather placed into the appropriate regions specially provided for them, incoming from a series of previously loaded containers.

A further advantage derives from the fact that the blister pack according to the present innovation enables an effective protection of the teeth from minor accidents; these always remain in their place, even in case of breaking or fall of the housing box.

Another further advantage derives from the fact that, once the need of the wax is overcome, problems of heat and of dust retaining cease to exist.

The advantage then of a box apt to house the packagings according to the present invention derives from the fact that this is much simpler and cheaper, as its protective function becomes less crucial.

Another advantage derives from the fact that replacing and/or tamperings of the teeth inside the sealed blister pack are not possible anymore.

Furthermore, with the blister pack according to the invention, the possibility of guaranteeing the quality and the technical features of the product by the manufacturer becomes much more practical, being therefore, as liable party, better protected.

Moreover, the simultaneous presence of the removable labels enables the complete elimination of possible mistakes that occur in the stage of indication of the ciphers composing the number marking the set of information that is to be reported mandatorily onto the documents or working forms. In fact, each user will obtain his copy of the lot number directly from the blister pack, with no need whatsoever of copying it, and then sticking or putting it into his own registers or working forms.

The present invention will be disclosed hereinafter in one of its preferred embodiments, given by way of example and not for limitative purposes. Reference shall be made to the figures of the further annexed drawings, wherein.

Figure 3:
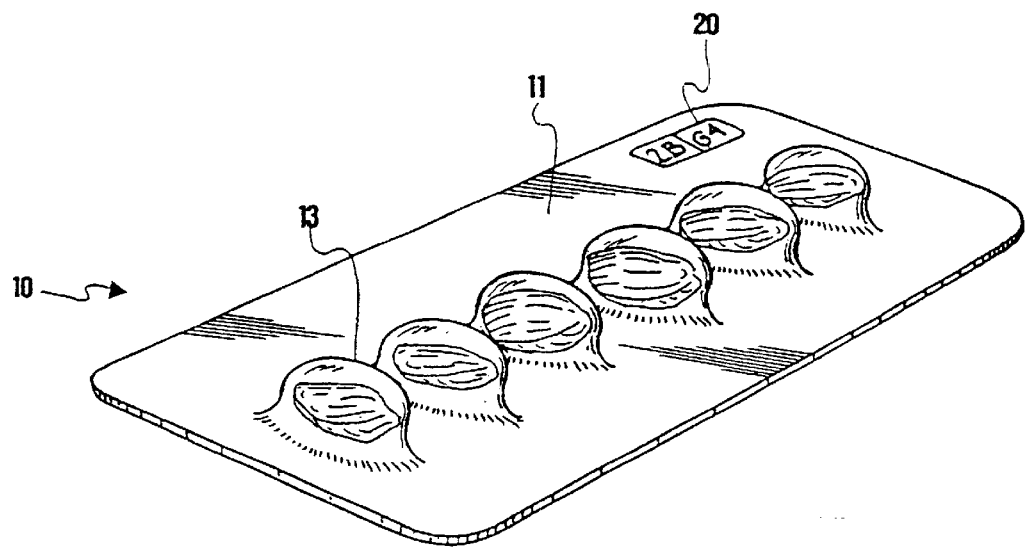
FIG. 3 shows a top perspective view of the blister pack according to the present invention.
Figure 4:
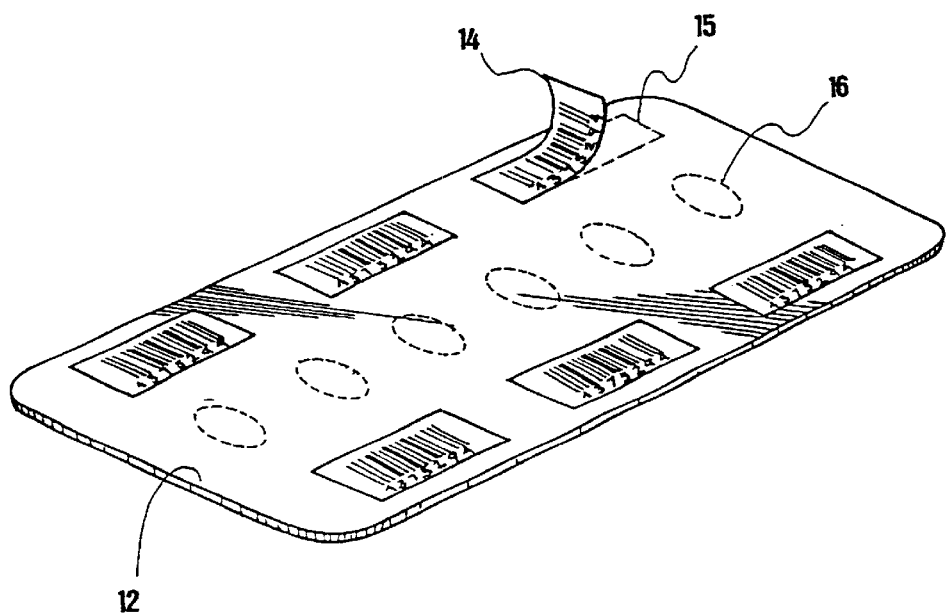
FIG. 4 shows a bottom perspective view of the blister pack according to the present invention.

FIGS. 3 and 4 show perspective views, top and bottom respectively, of the blister pack 10 according to the present invention. Such blister pack comprises first of all a first layer 11 preferably made of a transparent plastic material, apt to contain the artificial teeth 3 and to enable their view. Such first layer comprises in particular a plurality of raised regions 13 in the inside of which the artificial teeth 3 are housed.

Then, with reference to the next FIG. 4, a further second layer 12 can be seen, preferably realized in simple carton board or in rolled aluminium, placed below the first layer 11 and welded therewith. Such second layer, shown from a bottom view in FIG. 4, comprises a plurality of punching regions 16 apt to be punched with a pressure applied onto the raised regions 13. The punching regions 16 are shown as hatched in FIG. 4 purely by way of explanation, as they do not differ in constitution from the remaining portions of the second layer 12. Onto the lower face of the second layer 12 a plurality of removable elements 14 is present, identifying the blister pack, i.e. comprising the lot number of the same and, in case, a bar code. In the preferred embodiment of FIG. 4 such elements 14 are glued with an adhesive substance and placed along removal regions 15 of the second layer 12. In FIG. 4 the removal regions 15 are separated from the punching regions 16. However, it is possible to provide embodiments wherein a partial or total overlapping between regions 15 and 16 is present, as the removal of the removable elements 14 usually takes place prior to the utilisation of the artificial teeth by the dental technician or the dentist.

The removable elements 14 have been represented as identical one to each other in the preferred embodiment of the figure. However, embodiments can be provided wherein such elements are different therebetween, for instance realized with different colourings.

Figure 1:
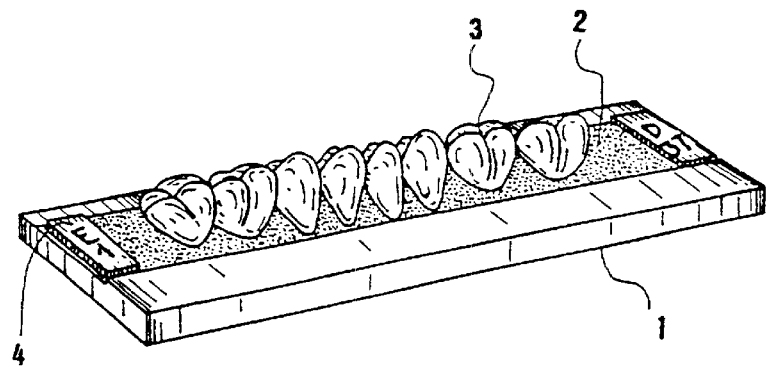
Figure 2:
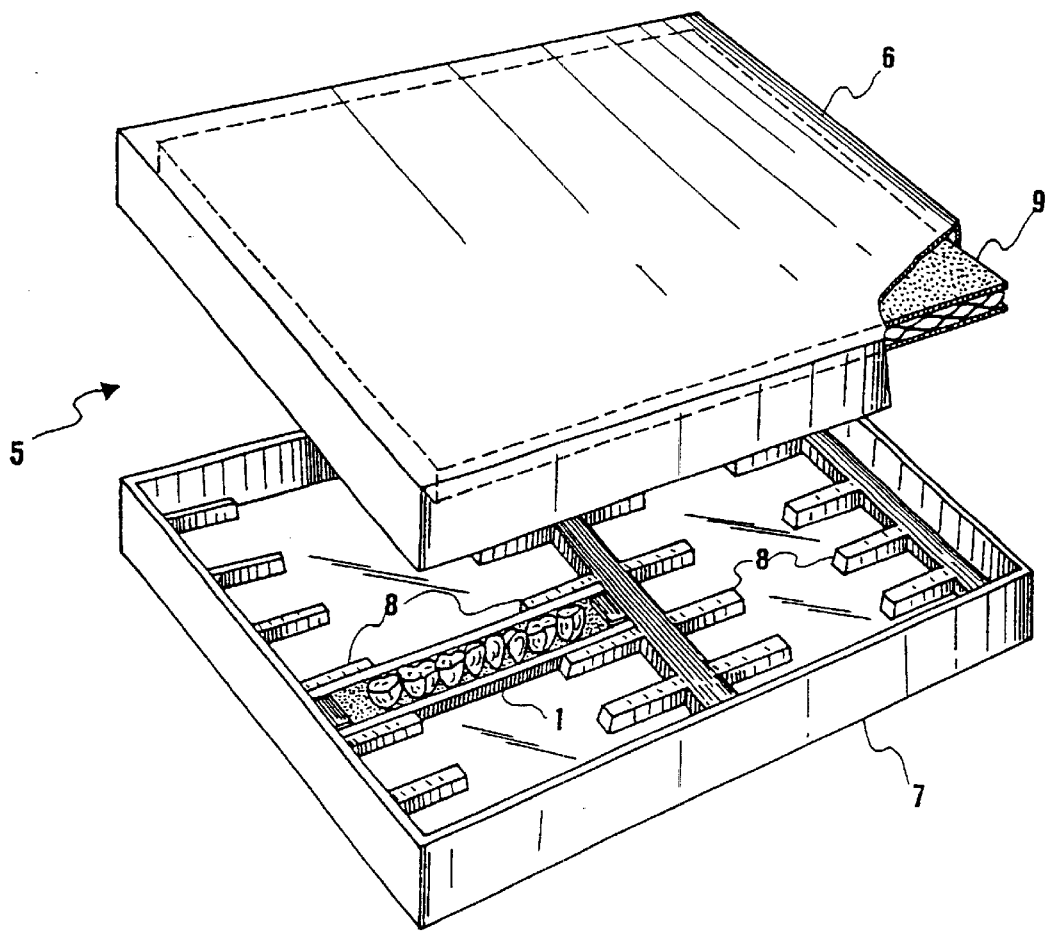
Figure 5:
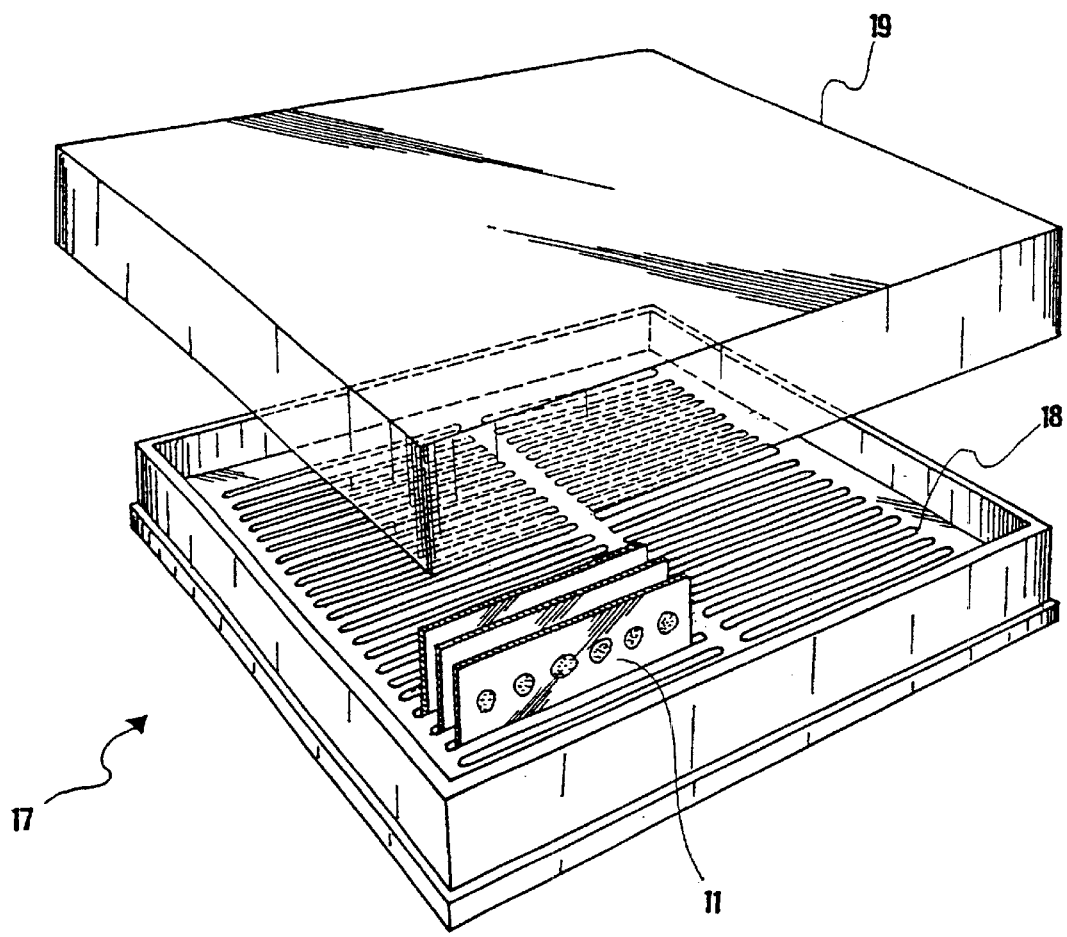
FIG. 5 shows a perspective view of a box apt to contain the blister pack according to the present innovation.

The next FIG. 5 shows a box 17 for the housing of a plurality of blister packs 10 according to what was hereto disclosed. Such box 17 comprises a respective plurality of housings 18, apt to house the blister packs 10. It is a peculiarity of the box at issue that of comprising a cover 19 realized in transparent material. The realization of a cover in a transparent material is in fact utterly unfeasible for the box 5 of previous art described with reference to the previous FIG. 2, as in such embodiment an element was necessarily provided, e.g. the wafer 9 in multilayered paper, apt to prevent the shifting of the strips 1 in a direction that is orthogonal to the plane of the box base. In the box of FIG. 5 instead, the presence of an element such as the wafer 9 is not at all necessary, given the peculiar blister pack of the artificial teeth hereto disclosed. The presence of the aforesaid cover 19 realized in transparent material entails various advantages, among which in particular the possibility of providing an optical identification (e.g. with a laser beam) with the box kept closed of the blister packs contained therein.

The invention has been hereto disclosed according to one of its embodiments, given by way of example, and not for limitative purposes. Hence, it is apparent that the embodiment variants introduced may be varied and different, all however comprised within the same protective scope. For instance, information identifying the teeth colour and shape can be provided, preferably placed onto the lower face of the first layer 11 or onto the upper face of the second layer 12 and shown with the number 20 in FIG. 3. Moreover, another alternative is given by the possibility of providing means for the electronical identification of the blister packs, for instance a microprocessor or a transponder.

The function of a transponder is supposed to be well known to the skilled person, and shall not be here described in detail. With the use of the transponder it will be possible to obtain any type of information remotely and using well known electronic components connected to a PC. Such information could for example relate to the number and the type of blister packs contained inside a box such as those of FIG. 5.

The transponder will be such as to comprise a radiofrequency antenna and a memory wherein the most significant information relative to the blister pack, i.e. code, serial number, shape and color of the teeth as well as any other data that might be necessary or useful for remotely identifying the blister pack will be stored. Furthermore it is to be considered that the transponder is re-writable and therefore is such as to allow the input of additional or different information.

A non limiting example of transponder is the 13.56 MHz transponder produced by the German company DTE Automation GmbH, having a square (45×45 mm) or rectangular (45×76 mm) antenna and comprising a 256 bit non-volatile memory which can be programmed by the user. Furthermore, the presence of a software allowing the simultaneous reading of a plurality of transponders can be provided.

A first setup mode of the transponder provides its application by means of an adhesive along the bottom part of the second layer, next to the removable elements 14. The advantage of said first mode is that of not having to change the -shape of the blister pack to take into consideration the presence of the transponder.

On the other hand, a second setup mode of the transponder provides a change in the shape of the blister pack, hence creating an additional region to contain the transponder. The advantage of said second mode is that of being however able to provide the presence of a number of removable elements 14 equal to the number of elements provided in the embodiment without the transponder.

With reference to FIG. 5, the different transponders will be applied in every blister pack in the upper regions thereof. Furthermore, from said FIG. 5 it can noticed that each blister pack is perpendicularly placed to the base of the box. Trials carried out by the inventor brought to the result that the best possible disposition of each blister pack provides a 450 inclination with respect to the base of the box, so as to minimize the risk of interference among the transponders.

A further alternative is given by the providing for the blister pack to be dissectable by means of weakening lines enabling the separation of single portions of packaged teeth from the remaining part of the blister pack.

What is claimed is:

1. A blister pack (10) of artificial teeth comprising:

a plurality of artificial teeth (3) of prosthetic use;

a first layer (11) for housing said artificial teeth (3), having a plurality of raised regions (13) in correspondence with said artificial teeth (3);

a second layer (12) placed below the first layer (11), comprising a plurality of punching regions (16) apt to be punched upon pressure onto the raised regions (13); and a plurality of removable elements (14) identifying the blister pack, placed onto the second layer (12).

2. The blister pack according to claim 1, characterised in that said first layer (11) is transparent.

3. The blister pack (10) according to claim 1, characterised in that said removable elements (14) are placed along removal regions (15) which are separated from the punching regions (16).

4. The blister pack according to claim 1, characterised in that said plurality of removable elements (14) comprises elements identical one to each other.

5. The blister pack according to claim 1, characterised in that it comprises information (20) identifying colour and shape of the teeth.

6. The blister pack according to claim 1, characterised in that it comprises means for enabling electronic identification of the same.

7. The blister pack according to claim 6, characterised in that said electronical identification means is a transponder.

8. The blister pack according to claim 1, characterised in that it comprises weakening lines for enabling separation of single portions of packaged teeth from the remaining part of the blister pack.

9. A box (17) of artificial teeth, comprising: a plurality of blister packs (10) of artificial teeth for prosthetic use according to claim 1, a respective plurality of housings (18) so as to house said blister packs (10); and a transparent cover (19) for enabling optical identification of said blister packs (10).

10. A box according to claim 9 comprising a box base and housing a plurality of blister packs characterised in that each of said blister packs is inclined of 45° with respect to said box base.

* * * * *

UNITED STATES PATENT AND TRADEMARK OFFICE
CERTIFICATE OF CORRECTION

PATENT NO. : 6,415,916 B1
DATED : July 9, 2002
INVENTOR(S) : Guido Rini

It is certified that error appears in the above-identified patent and that said Letters Patent is hereby corrected as shown below:

<u>Title page,</u>
Item [22], should read
-- [22], PCT Filed: July 16, 1999 --

Signed and Sealed this

Fourth Day of February, 2003

JAMES E. ROGAN
*Director of the United States Patent and Trademark Office*